United States Patent [19]
Ramarao

[11] Patent Number: 5,954,922
[45] Date of Patent: Sep. 21, 1999

[54] METHOD AND APPARATUS FOR DETERMINING PULP PERMEABILITY AND COMPRESSIBILITY FOR CONTROLLING PAPERMAKING PROCESS

[75] Inventor: Bandaru V. Ramarao, Dewitt, N.Y.

[73] Assignee: The Research Foundation of State University of New York, Albany, N.Y.

[21] Appl. No.: 08/865,783

[22] Filed: May 29, 1997

[51] Int. Cl.[6] .................................................. G01N 33/34
[52] U.S. Cl. ....................... 162/198; 162/252; 162/258; 73/53.03; 73/53.04; 364/471.01; 364/471.02
[58] Field of Search ................................... 162/198, 252, 162/254, 258, 261, 263, DIG. 10–11; 73/53.03, 53.04; 364/471.01, 471.02

[56] References Cited

PUBLICATIONS

Ramarao, B.V. and Kumar, P., "A Model for the Gravity Drainage of Papermaking Suspensions", Nordic Pulp and Paper Research Journal, vol. 11, No. 2, pp. 86–94, May 30, 1996.
Wei, H. and Ramarao, B.V., "Characterization of Pulp Slurries Using a Novel Drainage Tester", TAPPI Proceedings, pp. 517–523., Engineering Conference, Oct. 1996.
Unbehend, J.E., "Laboratory Drainage Testers—A Critical Review," Empire State Paper Research Institute, pp. 1–13 (1991).
Andrews, B.D. & White, L.R., "A Constant–Rate Rapid Drainage Tester," Tappi, vol. 52, No. 6, pp. 1171–1175 (1969).
Pires, E.C., Springer, A.M. & Kumar, V., "Computational model for water drainage in fourdrinier paper machines," Tappi Journal, pp. 133–139 (Apr. 1988).
Pires, E.C., Springer, A.M. & Kumar, V., "A new technique for specific filtration resistance measurement," Tappi Journal, p. 149154 (Jul. 1989).
Sampson, W.W. & Kropholler, H.W., "Batch–drainage curves for pulp characterization—Part 1: Experimental," Tappi Journal, vol. 78, No. 12, pp. 145–151 (1995).
Sampson, W.W. & Kropholler, H.W., "Batch–drainage curves for pulp characterization—Part 2: Modeling," Tappi Journal, vol. 79, No. 1, pp. 151–160 (Jan., 1996).
Raisanen, K, Paulapuro, H. & Maijala, A., "Effect of vacuum level and suction time on vacuum assisted drainage of a paper machine wire section," Appita, vol. 48, No. 4, pp. 269–274, (Aug., 1995).
Gess, J.M., "An Introduction To The G/W Drainage Retention System," Tappi Short Course—Retention and Drainage, pp. 49–52 (1989).

(List continued on next page.)

*Primary Examiner*—Peter Chin
*Assistant Examiner*—Steven B. Leavitt
*Attorney, Agent, or Firm*—Heslin & Rothenberg, P.C.

[57] ABSTRACT

Method and apparatus are presented for use in a papermaking process for determining permeability and/or compressibility characteristics of a pulp suspension within the process. The method/apparatus includes monitoring height of pulp suspension within one or more test columns as a function of time while allowing pulp suspension drainage from each test column. At least one parameter representative of permeability or compressibility of the pulp suspension is determined, via computer processing, using the monitored height as a function of time of the pulp suspension within the test column. The at least one parameter representative of permeability or compressibility can comprise specific surface area ($S_w$), specific volume ($v_f$) compressibility constant m or compressibility constant n for the pulp suspension. Further, a measure of the permeability and/or compressibility characteristic(s) of the pulp suspension attributable to fines in the pulp suspension is obtained using two test columns, each having a different size screen disposed therein to allow different size fibers of the pulp suspension to pass therethrough. The determined parameters are employed as control feedback to the papermaking process for maintaining one or more pulp suspension characteristics near a predefined set point.

24 Claims, 3 Drawing Sheets

OTHER PUBLICATIONS

"T 221 su–72—Drainage Time of Pulp," Standards Administrator, TAPPI, Atlanta, GA (2 pages), 1996.

Mantar, E, Co, A. & Genco, J.M., "Drainage Characteristics of Pulp Slurries Under Dynamic Conditions," Journal of Pulp and Paper Science: vol. 21, No. 2, pp. J44–J50 (1995).

Henrik, N., "Determination Of The Filterability Of Cellulose Fibre Suspensions," Svensk Papperstidning, No. 9, pp. 265–272 (1977).

Davis, K.E. & Russel, W.B., "An asymptotic description of transient setting and ultrafiltration of colloidal dispersions," Phys. Fluids A 1(1), pp. 82–100 (Jan. 1989).

Ramarao, B.V. and Kumar, P., "A Model for the Gravity Drainage of Papermaking Suspensions", Nordic Pulp and Paper Research Journal, vol. 11, No. 2, pp. 86–94, May 30, 1996.

Wei, H. and Ramarao, B.V., "Characterization of Pulp Slurries Using a Novel Drainage Tester", TAPPI Proceedings, pp. 517–523, Engineering Conference, (Oct., 1996).

fig. 1 fig. 2 fig. 3

METHOD AND APPARATUS FOR DETERMINING PULP PERMEABILITY AND COMPRESSIBILITY FOR CONTROLLING PAPERMAKING PROCESS

TECHNICAL FIELD

This invention relates in general to papermaking, and more particularly, to a method and apparatus for determining permeability and compressibility characteristics of pulp suspension, e.g., within a papermaking process. These determined characteristics are internally consistent and can be used to estimate drainage under varying pressure, consistency, temperature and composition conditions and also can be used for enhanced control of the papermaking process.

BACKGROUND OF INVENTION

Drainage of pulp is an important phenomenon operating during the papermaking process and in other situations where dewatering of pulp stocks is necessary. In most situations, it is necessary to characterize the dewaterability or drainability of pulp suspensions by using some measure. The principal purposes for which drainage testers have been used in the papermaking industry include: to evaluate pulp quality; to predict the paper machine drainage of a given furnish; to predict retention; and/or to predict pulp/paper physical properties such as strength and fiber flexibility.

The paper industry has traditionally sought a way to predict how changes in fiber (source and variation), refining, chemical additives and wet end conditions will effect the drainage of the papermaking furnish. The papermaking process is, in total, based on the separation of large quantities of water from fiber dispersed as a very dilute suspension. Thus, this knowledge would allow both the optimization of the dewatering process and a means of avoiding possible catastrophic upsets in the wet end system due to changes in the furnish components.

The importance of understanding the dewatering process has lead to the development of a number of devices to test, predict and monitor the drainage/dewatering process. These drainage testers usually rely on (a) measurement of drainage volume with time, (b) determination of specific filtration resistance, (c) determination of time to drain a certain volume under specific conditions, or (d) volume of water drained under specific conditions in a given time (see Unbehend, J. "A Critical Review of Drainage Testers," TAPPI Papermakers Conference (1991)). The following drainage testers are described in the literature:

1. Freeness testers (Canadian Standard Freeness, Schopper-Reigler)—see: "Drainage Time of Pulp," TAPPI Test Methods T221 su-72, TAPPI Atlanta Ga., (1996); El-Hosseiny, F. and J. F. Yan, "Mathematic Models for Freeness" Pulp Paper Mag., Can 81, 6, 61, (1980); and Swodzinski, P. C. and M. R. Doshi, "Mathematic Models of CSF and SR" TAPPI Intl. Process and Materials Quality Evaluation Conf. Proceedings, 253 (1986).
2. Dynamic drainage jar—see Penniman, J. G. and C. R. Olson, "Using the Britt Jar to Measure the Drainage" Paper Trade J., 34–36 (April 1979).
3. Turbulent sheet forming device—see Britt, K. W., J. Unbehend and R. Shridharan, "Observations on Water Removal on Papermaking" TAPPI 69, 7, 76–79 (1986).
4. Vacuum water release analyzer—see Britt, K. W., J. Unbehend and R.Shridharan, "Observations on Water Removal in Papermaking" TAPPI 69, 7, 76–79 (1986).
5. Specific filtration resistance tester see Pires, E. C., A. M. Springer, V. Kumar "A New Technique for Specific Filtration Resistance Measurement" TAPPI J., 149–153 (July 1989).
6. G/W drainage system—see Gess, J. M. "An Introduction to the G/W Drainage Retention System." TAPPI Short Course Notes on Retention and Drainage, 49–52 (1989).
7. Determination of beating degree—see Alfthan, G. V. "A Sensitive Apparatus for Rapid Determination of Beating Degree." Paper Ochtra, 6–7 (1976).
8. A tester based on constant rate rapid drainage—see Andrews, B. D. and L. R. White "A Constant Rate Rapid Drainage Tester." TAPPI J., 52, 6, 1171–1175 (1969).
9. Nisser's openness tester—see Nisser, H, "Determination of the Filterability of Cellulose Fiber Suspensions" Transl. from Swedish, Pulp and Paper Research Institute of Canada, Series No. 313 (1978).
10. The moving belt drainage tester—see Karrila, S., K. Raisanen and H. Paulopuro, TAPPI Papermakers' Conf. Proceedings, 275 (1992).

Notwithstanding the wide range of drainage testers described in the literature, as represented by the above-summarized techniques, all current testers and test methodologies suffer from two main disadvantages. First, the existing measurements are used in an empirical manner. Conventionally, the drainability measure or index represents some physical quantity which is monitored under a very specific experimental configuration and under very specific external physical conditions. The empiricism of these measurements means that they cannot be easily extrapolated to different conditions of pulp consistency, pressure or configurations. Secondly, although some of the measures purport to measure a more fundamental quantity for the pulps like the specific filtration resistance, they do so only under very specific conditions. These also suffer from the problem of not being true fundamental pulp properties and hence are not entirely useful for predictive or control purposes.

In other words, the parameters determined by the above-named testers are not fundamental parameters of a paper pulp. Whether it is the freeness (CSF or SR) or the time of drainage in a DDJ or the time taken under different vacuum conditions (turbulent sheet forming device or vacuum water release analyzer) or the specific filtration resistance tester, they each measure the properties of a pulp under a certain unique configuration. Therefore, extending the test results to a new situation or interpretation of the test results in terms of a pulp property is rendered difficult. The present invention addresses this difficulty by providing a new tester and testing methodology to determine the true characteristics of a papermaking pulp suspension. These characteristics may then be used to control various pulp processing operations.

DISCLOSURE OF THE INVENTION

Briefly summarized, this invention comprises in one aspect a method for controlling a papermaking process having a control variable and employing a pulp suspension. The method includes monitoring pulp suspension height as a function of time within a test column while allowing pulp suspension drainage from the test column; determining at least one parameter representative of permeability or compressibility of the pulp suspension utilizing the monitored height as a function of time of the pulp suspension within the test column, wherein the at least one parameter comprises one of a specific surface area ($S_w$), specific volume ($v_f$), compressibility constant m or compressibility constant n for the pulp suspension; and employing the at least one parameter representative of permeability or compressibility of the pulp suspension as a feedback to adjust a control variable of the papermaking process to maintain a pulp suspension characteristic near a predefined set point.

In another aspect, the invention comprises a computer-implemented method for determining at least one parameter representative of permeability or compressibility of a pulp suspension within a papermaking process. The method includes: monitoring instantaneous heights of pulp suspension within a test column under varying pressure conditions while allowing drainage of pulp suspension from the test column; and determining the at least one parameter representative of permeability or compressibility of the pulp suspension utilizing the monitored instantaneous heights. By way of example, the at least one parameter representative of permeability or compressibility of the pulp suspension might comprise one of a specific surface area ($S_w$), specific volume ($v_f$), compressibility constant m or compressibility constant n for the pulp suspension. In enhanced version, the method can comprise determining a difference in the at least one parameter between pulp suspensions in two different test columns having different size screens, wherein the screens are sized such that the difference is attributable to the fines in the pulp suspension.

In a further aspect, a method for characterizing fines in a pulp suspension of a papermaking process is provided. The method includes: providing at least two test columns having different size screens for removal of fibers from the pulp suspension, one of the screens being sized to allow fines to pass therethrough and one of the screens being sized to prevent fines from passing therethrough; establishing the pulp suspension within each of the two columns; monitoring instantaneous height of the pulp suspensions within the columns under varying pressure conditions while allowing drainage of pulp suspension therefrom; determining a value for a pulp suspension characteristic from the pulp suspensions in each of the at least two columns; and employing the pulp suspension characteristic values obtained to determine a difference parameter representative of the pulp suspension characteristic attributable to the fines content of the pulp suspension.

In another aspect, a test apparatus is presented for determining at least one parameter representative of permeability or compressibility of a pulp suspension. The apparatus includes a test column for containing the pulp suspension. The test column has a screen in a lower portion thereof for filtering fibers from the pulp suspension. A sensor is positioned adjacent the test column for monitoring height of the pulp suspension within the test column as a function of time while the pulp suspension drains from the test column. The sensor provides output signals, each being representative of the instantaneous height of the pulp suspension within the test column under a different pressure condition. Processor means are also provided which are coupled to receive from the sensor the output signals and determine therefrom the at least one parameter representative of permeability or compressibility of the pulp suspension. The at least one parameter comprises one of a specific surface area ($S_w$), specific volume ($v_f$), compressibility constant m or compressibility constant n for the pulp suspension.

To restate, a pulp tester and analysis method are presented herein which are capable of determining an optimal parameter set of $S_w$, $v_f$, m, n for a given pulp by analyzing its gravity drainage curve. This parameter set is unique. The set describes gravity drainage of the pulp under variation in consistency as well as gravity drainage configuration geometry (e.g., vessel heights, pressure differentials, etc.). The specific surface area strongly characterizes the permeability of the pulp. It drifts higher or lower depending on the flocculation state of the pulp. Thus, it can be used as an indicator measure of flocculation state—possibly tuning the retention or drainage aid dosages. The specific surface area also characterizes the drainage of refined pulps to different extents. Refining changes the area and thus surface area can also be used as a measure to control the operation of pulp refiners. Judicious application of the technique in a repeated fashion on pulps which are fractionated or which undergo fractionation results in a measure of the fines content of the pulp. The fractional surface area attributable to the fines fractions can be utilized in place of the mass basis fines fraction in many situations directly. Finally, it is possible to obtain a measure of the pulp's wet fiber flexibility (wet fiber elastic modulus) by measuring the compressibility parameters and suitably correlating them.

BRIEF DESCRIPTION OF THE DRAWINGS

The above-described objects, advantages and features of the present invention, as well as others, will be more readily understood from the following detailed description of certain preferred embodiments of the invention, when considered in conjunction with the accompanying drawings in which.

BEST MODE FOR CARRYING OUT THE INVENTION

Generally stated, this disclosure presents a novel technique for determining the characteristics of a papermaking pulp suspension. The characteristics obtained may be used to control various pulp processing operations.

An instrument in accordance with the present invention can determine various pulp characteristics, including: the hydrodynamic specific surface area $S_w$, the specific volume $v_f$, the compressibility of the pulp (which may be described by power law constants, m and n, or the wet fiber elastic modulus, $E_{wf}$) and the fractional specific surface area of the individual pulp fractions, such as fines. These parameters are determined by analyzing the rate of removal of water from the pulps under different conditions of pressure. Pulps are dewatered by a combination of gravity and pressure (or vacuum) and the dewatering rates are measured by ultrasonic or other ranging techniques to follow the movement of the pulp suspension—air interface. Dewatering under a range of conditions provides drainage data through a computerized data acquisition system.

Mathematical models of drainage, dewatering and filtration are applied with pulp characteristics, namely, the specific surface area, specific volume, and compressibility measures (i.e., either power law indexes m and n, or suitable viscoelasticity parameters) as inputs to the models. Best fitting model predictions to the experimental results are obtained by minimizing the sum of squares of the errors between the model predictions and the measured data. The optimal parameters so chosen represent the characteristic parameters for the pulps. These characteristic parameters are then used to control various pulp processing operations.

Figure 1:
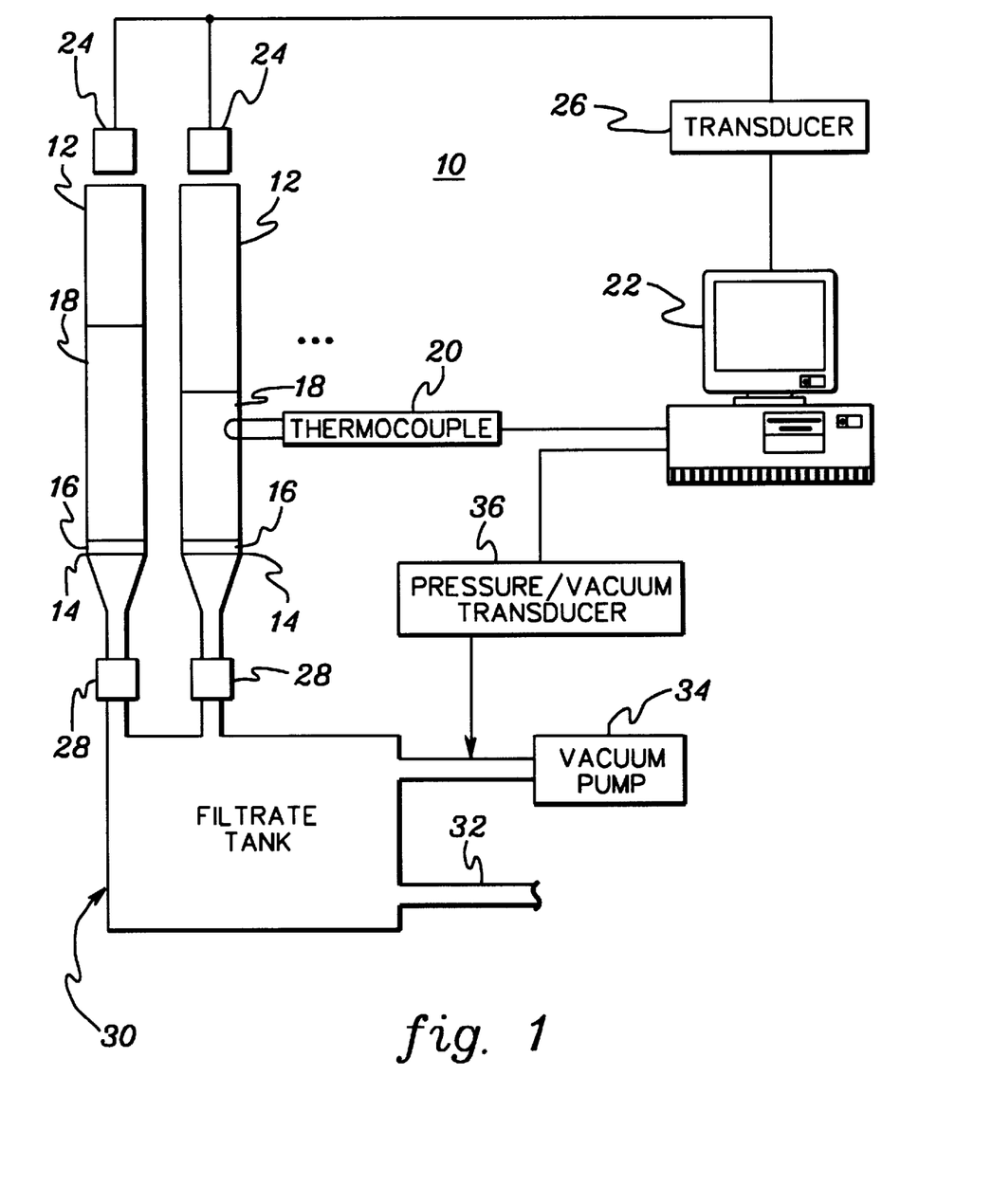
FIG. 1 is a diagram of one embodiment of a pulp suspension characterization instrument in accordance with the present invention.

One embodiment of a pulp suspension testing instrument, generally denoted 10, in accordance with the present invention is depicted in FIG. 1. Instrument 10 includes multiple drainage columns 12, each of which includes a machine screen 14 in a lower portion thereof. The machine screens employed within the drainage columns may allow the same or different sized filtrate to pass. For example, 100 mesh and 60 mesh screens may be used in the two different columns depicted. The multiple columns may each comprise plexiglass columns, at least one of which may include a thermocouple 20 for determining temperature of a pulp suspension 18 under test. Data from thermocouple 20 is fed to a processor 22 with an A/D board and computer code for processing data as described herein below.

Each drainage column is connected to a filtrate collection tank 30 through a respective control valve 28. Tank 30 also serves as a buffer for facilitating maintaining of constant pressure or a vacuum relative to the columns, for example, via a vacuum pump 34 with control feed back through a pressure/vacuum transducer 36 to processor 22. Filtrate is drained from tank 30 through an output port 32. Below each screen assembly, an air-bleed opening (not shown) would also be provided to aid in removal of air.

In accordance with one aspect of the present invention, a ranging system is provided which consists of an ultrasonic sensor 24 (e.g., Pulsonic Model—8800) affixed to a top plate over each column 12. The sensors 24 are connected to a power supply and a control unit. Transfer of data from sensors 24 to computer 22 can be through a conventional RS 232 interface. The entire drainage column-sensor assembly could be affixed to a platform and a vertical stand (not shown).

Operationally, the following test procedure can be employed. The valves at the bottom of each column are closed, the vacuum level is adjusted and water is placed in the base of each column until the water level reaches the height of wire screen 14. After the vacuum level reaches the desired steady state value, pulp suspension (e.g., one liter) is introduced into each drainage column after insuring that no air bubbles are entrapped in the region below the screen and above the check valve 28. The pulp suspension is kept in a stirred state, and at the start of the test, the check valve below each column is opened and the suspension is allowed to drain freely from the columns 12. In accordance with one embodiment of the present invention, the air-suspension interface level in the columns is continuously monitored by the ultrasonic sensors and the respective height versus time experimental data readings ($H_{exp}$) are acquired and stored for further processing as described below.

The temperature can be determined by a thermocouple provided as shown and the initial consistency of the pulp suspension can be determined and provided as an input to the data analysis program. As one example, this might be obtained by removing the pad formed on each wire screen, drying the pad in an oven overnight and weighing it. The dried pad weight would then be used to estimate the slurry consistency. At the conclusion of each test, the drainage column assemblies are unclamped, the pulp mats are removed, and the screens are cleaned.

With the ranging system described herein, the suspension height can be measured to an accuracy of 0.1 centimeters every ten milliseconds during the process of drainage. Thus, measurement of suspension height in each column is virtually continuous. This ensures an accurate measurement of drainage velocity, which is important for characterizing pulp slurries using drainage testers.

More importantly, in accordance with the present invention, determination of the height of the pulp slurry as a function of time or as a function of varying pressure conditions, is needed in order to determine an optimal parameter set which characterizes the pulp suspension.

Pursuant to this invention, a parameter (or more preferably, a set of parameters) is(are) determined to represent permeability and/or compressibility of the pulp suspension. These parameters can include specific surface area $S_w$, specific volume $v_f$, and compressibility of the pulp (which may be described by power law constants, m and n, or the wet fiber elastic modulus $E_{wf}$). As an enhancement, the fines composition of the pulp can also be determined, e.g., as a measure of a specific surface area attributable to the fines fraction $\Delta S_w$ using data from two different columns with different screen sizes. Pulp characterization procedures in accordance with this invention are next described. Note that with respect to the following discussion, analysis of drainage data can be performed either while the test is being conducted (i.e., in an online implementation) or in an offline test embodiment. Further, analysis of drainage data can be performed as the data is received or upon conclusion of the testing after all drainage data has been collected. The analysis is performed by utilizing a novel model for gravity and pressure drainage as follows.

As noted, in accordance with this invention, instantaneous filtration measurements of pulp are obtained under varying pressure conditions. Varying pressure can be achieved by monitoring gravity drainage over time or by the application of a vacuum using a computer controlled solenoid valve as presented above. In addition to determination of water flux, i.e., drainage rate as a function of time accurately; measuring temperature, consistency and external parameters including resistance of flow apparatus can also be employed.

Pursuant to the present invention, a response variable is determined by monitoring (in one embodiment) height of the pulp suspension as a function of time. More broadly stated, the parameters are determined by monitoring the pulp suspension under varying conditions such as changing pressure. As one embodiment, the parameters to be simultaneously determined as representative of the permeability and compressibility of the pulp are specific surface area, $S_w$, specific volume $v_f$, compressibility constant m and compressibility constant n.

Before describing Applicant's process in detail, the following symbol definitions are provided:

| | |
|---|---|
| $H_{th}$ | Height of suspension in column determined from mathematical model |
| $H_{exp}$ | Height of suspension measured from drainage column |
| t | Time, s |
| $S_w$ | Specific surface area, cm²/g |
| $v_f$ | Specific volume, cm³/g |
| m, n | Compressibility parameters, cgs units |
| $X^2$ | Objective function used for minimization |
| N | Number of experimental measurements |
| $\Delta S_w$ | Specific surface area attributable to |

-continued

| | |
|---|---|
| | fractions (fines) |
| L | Height of mat as it is building up inside column (model estimate) |
| $\rho_s$ | Density of suspension, g/cc |
| $\rho$ | Density of liquid, g/cc |
| g | Acceleration due to gravity |
| $r(c_{av})$ | Specific filtration resistance at $c_{av}$ |
| $c_{av}$ | Average consistency |
| $R_m$ | Resistance of screen and other flow internals |
| $H_0$ | Initial height of suspension |
| $k_z$ | Kozeny Carman constant |
| $\mu$ | Viscosity |
| $p_s$ | Pressure in the solid phase |
| v | Fluid velocity (= dH/dt) |
| $H_k$ | Vacuum or suction head |
| u | Drainage rate (= v above) |
| $\alpha L$ | Specific filtration resistance (r above) |
| $N_{exp}$ | Number of experiments |
| c | consistency |
| $\underline{x}$ | A vector representing ($S_w$, $v_f$ m, n) |

$N_{100}$, $N_{400}$ Integers representing total number of points, iterations etc. in algorithm

| | |
|---|---|
| $R_k$ | Uniformly distributed random numbers (Interval given adjacent to R) |
| $\mu'$ | Comparison fraction (Step 17 below) |
| $\Delta$ | Fraction (= 0.1) (defined in Step 20 below) |
| T | Annealing temperature (Function defined in steps 11, 21 and 22 below) |
| $c_o$ | Initial consistency |
| $\underline{x}^L$ | Lower Limit vector $\underline{x}$ |
| $\underline{x}^u$ | Upper Limit vector $\underline{x}$ |

The response variables to be estimated in accordance with this invention can be, for example, suspension height $H_{exp}$ or resistance $\alpha L_{exp}$, wherein $H_{exp}$ equals the height of suspension measured from the drainage column, and $\alpha L_{exp}$ equals the measured specific filtration resistance. The variable $H_{exp}(t)$ is measured directly by closely monitoring the drainage rate, while the variable $\alpha L_{exp}(t)$ can be determined by equations (1) & (2).

$$\alpha L_{exp}(t) = \frac{[H_{exp}(t) + H_k]\rho g}{\mu u(t)} - R_m \quad (1)$$

$$u(t) = \frac{d H_{exp}(t)}{dt} \quad (2)$$

Two different approaches to determining the desired parameters from the experimental data are described below. The first approach employs the suspension height as the response variable, while the second utilizes specific filtration resistance. Those skilled in the art will recognize that other response variables could also be employed to determine the desired parameters representative of the pulp suspension.

In accordance with one aspect of this invention, an estimate of the height of the pulp suspension ($H_{th}$) as a function of time is employed to establish pulp characteristics, namely, $S_w$, $v_f$, m and n. Thus, $$H_{th}(t) = H_{th}(t; S_w, v_f, m, n) = x \quad (3)$$

As noted in equation (3), the height of the pulp suspension is to be calculated theoretically as a function of time assuming values for $S_w$, $v_f$, m and n. One approach for determining the theoretical height is described in detail in an article by Ramarao & Kumar entitled "A Model for the Gravity Drainage of Papermaking Suspensions," Nordic Pulp and Paper Research, Journal No. 2, pp. 86–94 (May 30, 1996), which is hereby incorporated herein by reference in its entirety. Once the theoretical height versus time values are determined, the an objective function, labelled $X^2$, is determined as follows:

$$X^2 = \sum_{i=1}^{N_{exp}} [H_{exp}(t) - H_{th}(t)]_i^2 \quad (4)$$

wherein $N_{exp}$ equals the number of experimental readings, which by way of example, may be in the range of 100 to 500 experiments.

After calculating the objective function, the next step in this process is to change the assumed parameters of vector x to new values and obtain a new objective function $X^2$. The next vector values can be selected using the same approach as described herein below in connection with processing of the alternate response variable, i.e., specific filtration resistance ($\alpha L$). The problem is then to solve for Min[$X^2$] to obtain an optimal parameter set $S_w$, $v_f$, m, n by determining the best fitting model prediction to the experimental measurements. This is accomplished by minimizing the sum of squares of the errors between the model predictions and the measured data. In accordance with this invention, the optimal parameters so chosen are the characteristic parameters for the pulp suspension.

By way of more detailed discussion, the alternate approach for determining the parameters using the specific filtration resistance response variable would be as follows:

1. Determine $\alpha L_{exp}$ from $H_{exp}$ using equation (1).
2. Determine $\alpha L_{th}$ from:

$$\alpha L_{th} = \frac{(H_{th} + H_k - L)\rho g}{\mu u} - R_m \quad (5)$$

with $L = \frac{(H_o - H)c_o}{(c_{av} - c_o)} \quad (6)$

Where $c_{av}$ may be determined as described in the above-incorporated article by Ramarao & Kumar.

3. Determine $$X^2 = \sum_{i=1}^{N_{exp}} [(\alpha L)_{th} - \alpha L_{exp}]_i^2 \quad (7)$$

4. Solve the problem

Min $X^2$ $[\underline{x} = S_w, v_f, m, n]$

5. The minimization problem described on the previous page can also be solved by applying the algorithm described below. To applicant's knowledge this algorithm is unique. It comprises a case specific modification of the classical simulated annealing algorithm based on the Metropolis algorithm.

6. Let $X^2[\underline{x}]$ be a separate algorithm which determines the response function, given a value for each of $x = S_w$, $v_f$, m, n.

7. Choose $N_{100} \rightarrow$ an integer.

8. Choose $x^2 \rightarrow$ an initial guess for x.
9. Determine the vector parameters $x^j$, $j=1, \ldots N_{100}$ at random from an initial interval of $[x^L, x^u]$.
10. Use the vector parameters to determine the objective functions $X^2[x^j]$, $j\ 1, \ldots N_{100}, = X_j^2$
11. Determine $$T_{old} = \langle X_j^2 \rangle = \frac{1}{N_{100}} \sum_{j=1}^{N_{100}} X_j^2$$

and $X_{min0}^2 = \text{Min}\,[X_j, j = 1, \ldots N_{100}]$ wherein 'T' is employed to track how the processing is progressing towards a minimum.

12. Choose $k=1, \ldots N_{400}$; $x^{old}=x^o$ from step (8)
13. Determine $x_k^{new}=x_k^{old}+(\Delta x)\cdot R_k[-1,1]$ wherein $R_k[-1,1]$ is a uniform random number over the interval $[-1,1]$
14. Determine the object function $X_k^2[x_k^{new}]$.
14a. If $X_k^2 > X_{k-1}^2$, then calculate:

$$Z = \exp\left[\frac{X_{k-1}^2 - X_k^2}{T}\right]$$

Upon completion of steps (1)–(23), min $[X^2]$ is solved and an optimal parameter set, e.g., $S_w$, $v_f$, m, n, is determined by the best fitting model prediction to the experimental measurements. The optimal parameter set can then be employed to control the papermaking process as described below.

By repeating the optimization of parameters to minimize the deviations between experimental and theoretical heights for two different columns in succession, each having a different screen size, the surface area of the pulp suspension can be obtained, and also the specific surface area of the suspension fraction with fibers of size which are retained by the screen in the second column. The difference between the two, i.e., $\Delta S_w$, is a measure of the specific surface area attributable to the fines fraction. This value can further be used to characterize the contribution of the fines to sheet opacity, scattering properties and/or strength properties.

In essence, determination of fines content would involve conducting the above steps (1)–(23) for each column of the tester, assuming that each column is fitted with a different screen to allow different size particles to flow through. By comparing the parameters obtained from the two columns (or from 3 or more columns) the contribution of fines to each parameter can be determined. For example, the measure of the specific surface area attributable to the fines fraction would be as set forth in equation (8)

$$\Delta S_w^{fines} = S_w^{w/fines} - S_w^{w/o\ fines} \tag{8}$$

wherein the $\Delta S_w^{fines}$ is an important parameter in the papermaking process.

It is also possible to determine the specific filtration resistance or the permeability of the pulp as a function of time using the equations described above. The variation of the specific filtration resistance with time can also be compared with estimates from the theoretical model. The deviation between the theoretical estimates and the experimental measurements can be construed to be the magnitude of the viscoelastic affect of the pulp. This viscoelastic affect is a function of the fines content in the pulp besides other quantities. Finally, it is possible to use the compressibility constants m and n, as measures of the compressibility or even the wet fiber elastic modulus $E_{ws}$. Those skilled in the art will be able to obtain the wet fiber elastic modulus as a function of the compressibility constants m and n.

To summarize, the technique presented herein is to solve equation (1) using a modified Runge-Kutta algorithm. A high order (6 or more) with high accuracy is used with a variable time step. At each function call where the derivatives are evaluated, the average concentration in the mat height, L, is monitored for convergence by iterating using a variation of the fixed point scheme. Convergence of the equations to fairly tight tolerances is required. The final numerical algorithm should satisfy the following requirements:

1. It should be robust. Note that a mathematical singularity in the equations exists for n values very close to 0.5. The algorithm should check and alter n value guesses which are exactly 0.5 or are sufficiently close by stepping around the singularity.
2. The algorithm should return a numerical solution for any combination of the four parameters within reasonable bounds subject to 1. The bounds are: specific surface area 1000 to 100000 $cm^2/g$; $v_f$ 0.5 to 4.0 cc/g; m 0.0001 to 0.003; and n 0.1 to 0.6.
3. Convergence of the algorithm for various parameter values should be established. An empirical manner of establishing convergence is to show that the solution variation decreases monotonically over a suitable interval of the time steps, e.g. [0.001, 1.0].
4. It is often necessary to use a stiff equation solver which will adjust the time step as the scale of the problem changes with time.
5. The algebraic equations should provide a unique converged solution at each time step. This should be monitored by using a rigorous tolerance check and iterating with appropriate guesses if necessary.
6. The optimization technique should return a unique set of parameters for a given experimental data set. This should correspond to the objective function being a global minimum at this point. A robust optimizer which can negotiate through numerous local minima is necessary. [The optimizer in our case is composed of a robust Simulated Annealing Technique using the Metropolis algorithm.]

Control of the pulp processing and papermaking operation is next discussed.

Refining of pulps is done conventionally to improve the bonding and other properties of pulps. The refining operation consists of forcing the pulp suspension inside a narrow gap between two disks which are rotating opposite to each other. The disks have serrations and bars cut into their surfaces to provide added turbulence and increase the beating action on the fibers.

It is known in the literature that refining of a pulp results in increased specific surface area besides changing the specific volume and other parameters. The changes are primarily due to fibrillation of the fibers internally and externally. Fibrillation contributes to increased flow resistance because the fiber surfaces are roughened and some portions of the cell wall may be disrupted. This usually translates into an increased specific surface area of the refined fibers as compared to the unrefined fibers.

Refining action also generates fine particles, i.e., portions of the cell wall which have detached themselves or small fibers which have been cut by the action of the refiner disks. Thus, the fines fraction increases during refining. Another effect on refining is that the fibers swell due to additional water inhibition and leaching out of some residual lignin from the pulping and bleaching operations. Both of these effects can be well characterized by a tester in accordance with this invention. The fines fraction can be monitored by the additional surface area generated, $\Delta S_w$, and the specific volume $v_f$ measures the swelling of the pulp.

Figure 2:
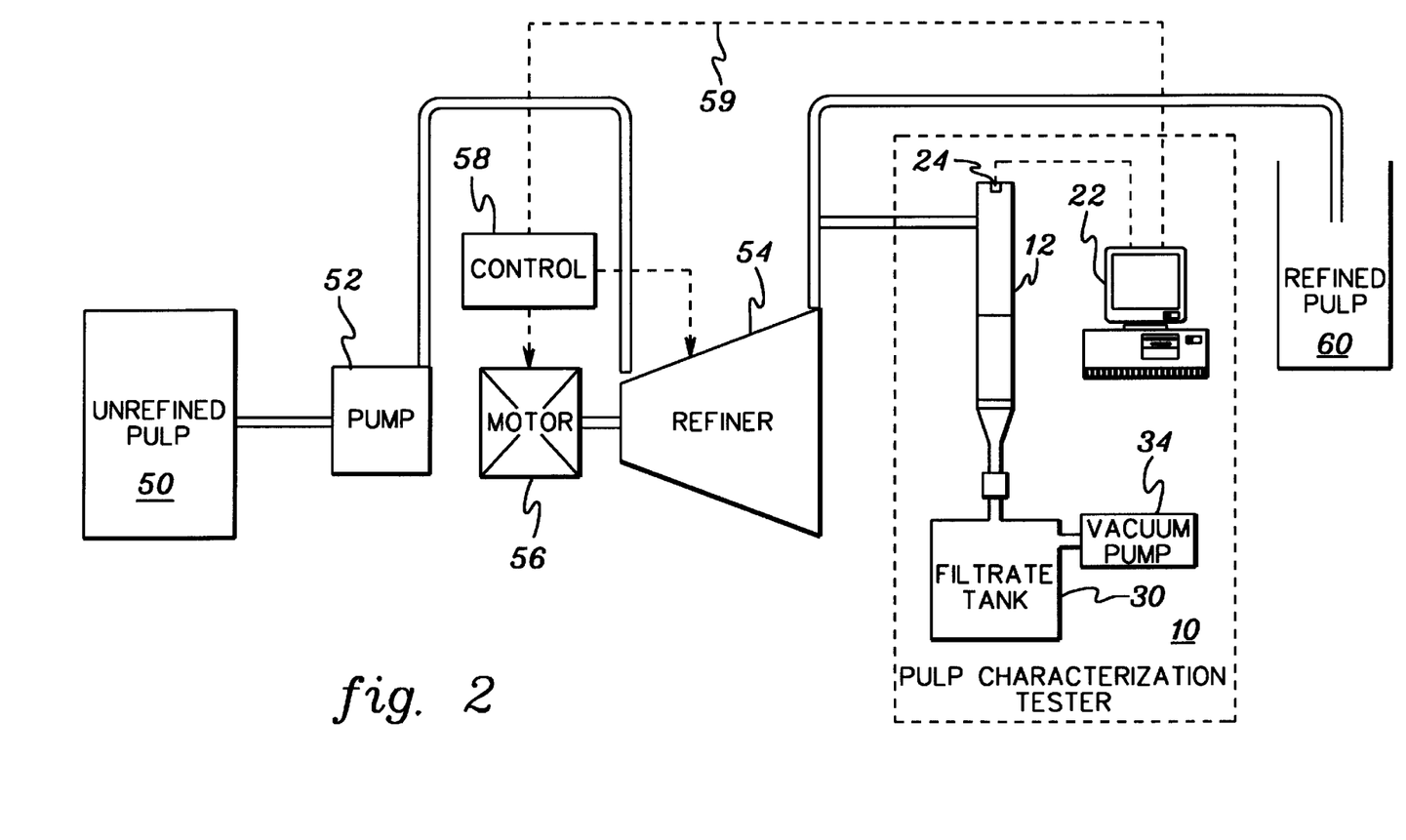
FIG. 2 is a diagram of one embodiment of a papermaking system employing the pulp suspension characterization instrument of FIG. 1 to control the papermaking process.

FIG. 2 depicts a schematic view of how a pulp suspension tester in accordance with the present invention can be employed to control the refining operation of the papermaking process. It is possible to control the refiners during stock processing using the data derived from pulp testing instrument 10. The unrefined pulp 50 is pumped 52 to a refiner 54. Refiner 54 is powered by a motor 56 which may be variably controlled 58 via a feedback line to the computer processing 22 of the pulp tester 10. Output from refiner 54 is to a refined pulp container 60 and also, for example, to column 12 of an automated tester in accordance with this invention.

In the example shown, the pulp stock is sampled after the refiner by drawing out a certain volume into multiple drainage columns, only one of which is depicted. Thereafter, the drainage is conducted and the height variation of time is measured. The optimal parameters $S_w$, $v_f$, m and n are determined from the experimental data as described in detail above. Furthermore, a measure of the fines production, $\Delta S_w$, is also obtained. With this information, feedback control of the papermaking process is possible.

For example, by determining deviation from a predefined set point, it is possible to control one or more parameters of the papermaking process. One could use a simple proportional-integral-derivative control procedure to generate the desired control signal. The control signal could be used (for example) to change the power input to the refiner, the refiner blade gap, the RPMs of the refiner or the specific edge loading to bring the refining action back to a predefined set point or range.

The addition of functional additives such as flocculants, defoamers, retention aids and drainage aids can also be accomplished in a similar fashion. The procedure is the same as described above except that the control variable would now represent the flow rate or concentration of additives instead of the power input. For instance, when an optimal dosage of a polymeric aid retention system is reached, the specific surface area shows a minimum. Further addition of polymer results in redispersion of the stock and a negative effect on drainage.

This system can also be utilized to determine the relationship between paper properties in terms of strength, light scattering and others, utilizing the specific pulp properties noted above. Thus, the system can be used to troubleshoot a situation where the quality of the final product undergoes a change by assigning the cause to either the pulp going to the production operation or the papermaking process variables themselves such as retention, etc.

The gravity drainage curves obtained experimentally for a variety of pulps have been analyzed as set forth in the examples below to establish optimal parameter settings consisting of their specific surface area $S_w$, specific volume $v_f$ and the compressibility parameters m and n. These parameters have then been studied to confirm that they are a meaningful description of the pulp's permeability and compressibility characteristics by determining their variation with pulp processing variables.

1. Optimal sets for various chemical softwood pulps and comparison with Pulmac Parameters. A set of gravity drainage data is provided in Table I along with pulp characteristics for a variety of chemical pulps using the above instrument.

TABLE I

| Pulp | $S_w$ | $V_f$ | m | n |
|---|---|---|---|---|
| BKE-R0 | 18,400 | 0.80 | 0.0032 | 0.32 |
| BKE-R5000 | 32,016 | 1.38 | 0.0039 | 0.33 |
| PAS-R0 | 13,224 | 0.84 | 0.0054 | 0.25 |
| PAS-R2000 | 14,725 | 0.95 | 0.0036 | 0.34 |
| PAS-R4000 | 18,870 | 1.02 | 0.0042 | 0.30 |
| PAS-R6000 | 24,646 | 1.28 | 0.0049 | 0.26 |
| PAS-R8000 | 30,710 | 1.37 | 0.0050 | 0.26 |
| PAS-R10000 | 35,263 | 1.55 | 0.0053 | 0.26 |
| SP-R0 | 8,091 | 1.40 | 0.0078 | 0.28 |
| SP-R10000 | 37,960 | 2.60 | 0.0072 | 0.26 |
| DSGW-0 | 24,000 | 2.4 | 0.0065 | 0.15 |
| DSGW-5 | 32,400 | 2.4 | 0.0065 | 0.18 |
| DSGW-10 | 40,800 | 2.4 | 0.0050 | 0.18 |
| DSGW-20 | 57,600 | 2.5 | 0.0070 | 0.20 |

Pulp Types: BKE—Bleached Kraft Eucalyptus, PAS—Prince Albert Softwood, SP—Southern Pine Kraft Pulp, DSGW—Headbox furnish containing stone groundwood. (–0, 5, 10, 20 represent % wt of fines in stock as fractionated in a DDJ). Redefining Levels (Revs in PFI Mill)—RO—Unrefined, Rx—Refined to 'x' revolutions.

These data were obtained using a single drainage column as opposed to the twin columns described above. Table II shows the optimal parameter sets obtained by analyzing the gravity drainage curves for additional pulps.

TABLE II

| Pulp | $S_w$ | $V_f$ | m | n |
|---|---|---|---|---|
| Puget Prime | 21,000 | 1.35 | 0.0015 | 0.380 |
| * | 25,837 | 1.37 | 0.00173 | 0.421 |
| Prince Albert W | 59,000 | 1.35 | 0.00076 | 0.462 |
| * | 59,879 | 1.35 | 0.00074 | 0.501 |
| Prince Albert D | 27,000 | 1.22 | 0.00114 | 0.440 |
| * | 28,515 | 1.22 | 0.0081 | 0.497 |
| Prince Albert 2 | 21,400 | 1.1 | 0.00140 | 0.40 |
| * | 21,400 | 1.1 | 0.00140 | 0.40 |

Wherein '*' represents data obtained from Pulmac Apparatus (An independent permeability—compression cell experiment.)

It is possible to measure these permeability and compressibility characteristics by using a flow through permeability tester in conjunction with a compression permeability cell. The instrument known as the Pulmac permeability tester has been used to determine the specific surface area, specific volume and compressibility constants for some pulps. Among the many problems associated with this instrument are the difficulty of obtaining reproducible measurements and reliable data. A comparison with the parameters as obtained by a Pulmac permeability tester is also given in Table II. We can see that in all the cases, the gravity drainage parameters are in rough agreement with the Pulmac results. It is important to realize that the Pulmac measurement is difficult to achieve and subject to significant error besides the compressibility being measured over a significantly higher loading condition.

Figure 3:
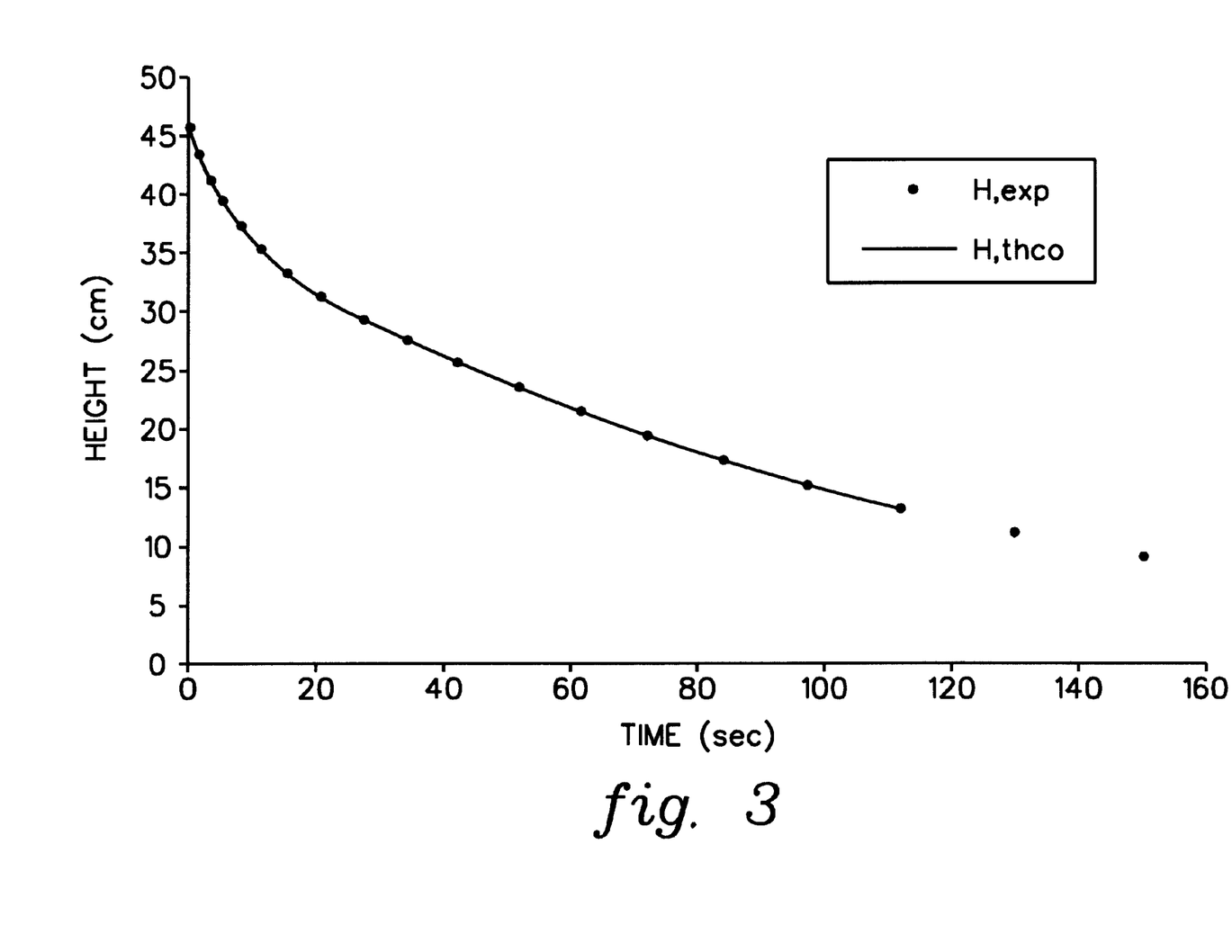
FIG. 3 is a graphical comparison of suspension drainage estimates using best fitting parameters of a theoretical height versus time model compared with experimental measurements of height versus time utilizing the pulp suspension characterization instrument of FIG. 1.

A comparison of the estimates of the drainage curves using the optimal parameter set and actual experimental data in accordance with the present invention is shown in FIG. 3. It can be seen that the experimental data is closely followed by the predictions from the optimal parameter set.

2. Description of gravity drainage curves under different external conditions (height and consistency). Table III shows the gravity drainage measurements from a column draining with three different initial heights. In this table, pulp parameters were measured by drainage of a chosen pulp (Prince Albert Softwood) at different consistencies and volumes (heights).

TABLE III

| H, cm | c, % | $S_w$, cm²/g | $v_f$, cm³/g | m, CGS units | n |
|---|---|---|---|---|---|
| 55 | 0.7 | 28,000 | 1.0 | 0.00130 | 0.41 |
| 40 | 0.7 | 28,000 | 1.0 | 0.00136 | 0.40 |
| 28 | 0.7 | 28,000 | 1.0 | 0.00136 | 0.40 |
| 55 | 0.5 | 28,000 | 1.0 | 0.00136 | 0.40 |
| 40 | 0.5 | 28,000 | 1.0 | 0.00130 | 0.41 |
| 28 | 0.5 | 28,000 | 1.0 | 0.00136 | 0.40 |
| 55 | 0.3 | 28,000 | 1.0 | 0.00106 | 0.45 |
| 40 | 0.3 | 28,000 | 1.0 | 0.00118 | 0.43 |
| 28 | 0.3 | 28,000 | 1.0 | 0.00124 | 0.42 |

By the close fit of the optimal predictions with the experimental data, it is evident that from the optimal parameter set obtained by analyzing one experimental data set, it is possible to estimate the drainage for other column heights. Similarly, the experimental measurements for different consistencies are predicted closely by a single optimal data set. This establishes that one singular optimal data set can indeed be obtained by analyzing the gravity drainage curves in one situation in accordance with this invention, and that this data set can effectively describe the variation with consistency, column height and other external parameters.

3. Variation of parameters with refining levels. The variation of the optimal parameters as a function of pulp refining level is shown in Table IV.

TABLE IV

| Pulp | W | $S_w$ | $v_f$ | m | n | CSF, ml |
|---|---|---|---|---|---|---|
| PA-0 | 0.424 | 17,700 | 1.1 | 0.00140 | 0.40 | 650 |
| * | 0.424 | 21,400 | 1.1 | 0.00140 | 0.40 | 680 |
| PA-1 | 4.58 | 41,500 | 1.1 | 0.00138 | 0.40 | 390 |
| PA-2 | 6.16 | 60,400 | 1.15 | 0.00137 | 0.41 | 230 |
| PA-3 | 7.3 | 74,500 | 1.12 | 0.00136 | 0.40 | 156 |
| PA-4 | 9.5 | 90,000 | 1.1 | 0.00140 | 0.42 | 105 |

Wherein the pulp parameters were obtained by gravity drainage for a set of pulps refined to different levels. W=the mass fraction of fines passing through 150 mesh.

From this table, it can be seen that the specific surface area increases with pulp refining. The specific surface area shows a steady increase with refining also. However, there is no effect on the compressibility parameters.

4. Variation of parameters with electrolyte content. Table V shows the parameters for a Puget Prime Softwood pulp flocculated by using NaCl as an electrolyte to collapse the electrical double layer between the fibers.

TABLE V

| Pulp | $S_w$ | $v_f$ | m | n | CSF |
|---|---|---|---|---|---|
| PP-0 | 21,000 | 1.35 | 0.00150 | 0.380 | 625 |
| * | 25,837 | 1.37 | 0.00173 | 0.421 | 657 |
| PP-1 | 16,000 | 1.30 | 0.00180 | 0.360 | 678 |
| * | 17,814 | 1.30 | 0.00183 | 0.417 | 685 |
| PP-2 | 15,000 | 1.27 | 0.00180 | 0.360 | 688 |
| * | 16,500 | 1.27 | 0.00182 | 0.418 | 695 |
| PP-3 | 14,500 | 1.20 | 0.00180 | 0.400 | 693 |
| * | 15,542 | 1.19 | 0.00174 | 0.425 | 696 |

Wherein Pulp Parameters were obtained from drainage curve analysis and Pulmac measurements. Puget Prime Softwood pulp flocculated by the addition of different levels of electrolyte (0,1,2,3—NaCl at 0, 0.001, 0.01, 0.1M, respectively). CSF for each of PP-0, 1, 2, 3 represents estimated CSF from the drainage parameters using the theory of Kumar et al. (1996). '*' Represents Pulmac measurements and actual experimental value of CSF.

The pulp was washed with dilute HCl to obtain its acid form. Three different levels, 0.001M, 0.01M, 0.1M were used in addition to the untreated pulp itself. We observe from this table that the specific surface area decreases indicating higher permeabilities and increasing drainage rates upon flocculation. Simultaneously, a small deswelling effect on the pulp fibers caused by osmotic pressure effects is also shown by the slow decrease in the specific volume of the fibers. We note that the compressibility parameters are scantily effected by the electrolyte or flocculation process itself. Another interesting observation is that the addition of electrolyte causes the flocculation, although the flocculation is not in direct proportion to the electrolyte added. Thus at high electrolyte levels, the reduction in specific surface is minimal. These results are in line with conventional understanding of flocculation brought about by the reduction in repulsive electrical double layer interactions due to the addition of counterions into the systems as per the DLVO theory of colloid stability. In Table V, we also show the corresponding Pulmac measurements which indicate much the same trends. These lend confidence to the optimal parameter sets obtained by gravity drainage analysis as shown herein, indicating that they can be used to follow electrolyte flocculation effects.

5. Variation of Parameters with Flocculation: Action of a Dual Polymeric Retention Aid System. We also considered the action of a dual polymeric retention aid system in bringing about flocculation. Table VI shows the effect of addition of Poly DADMAC (a high charge density, medium low MW cationic polymer) added to Prince Albert Softwood (kraft) pulp.

TABLE VI

| Pulp | $S_w$ | $v_f$ | m | n | CSF |
|---|---|---|---|---|---|
| WPA-0 | 82,000 | 1.18 | 0.00078 | 0.461 | 204 |
| * | 81,747 | 1.18 | 0.00079 | 0.502 | 405 |
| WPADD | 63,000 | 1.20 | 0.00091 | 0.458 | 292 |
| * | 63,470 | 1.20 | 0.00083 | 0.497 | 448 |
| WPA2AP | 60,000 | 1.26 | 0.00104 | 0.448 | 287 |
| * | 59,339 | 1.26 | 0.00095 | 0.484 | 457 |
| WPA1AP | 50,500 | 1.35 | 0.0010 | 0.450 | 369 |
| * | 48,997 | 1.35 | 0.00089 | 0.492 | 480 |
| WPA5AP | 57,500 | 1.35 | 0.0010 | 0.451 | 313 |
| * | 57,401 | 1.35 | 0.00089 | 0.493 | 475 |

Wherein Pulp Parameters determined by optimal drainage curve analysis, Prince Albert Softwood (Bleached Kraft). Pulp flocculated by addition of PolyDADMAC followed by Anionic Poly Acrylamide (APAM). DADMAC—(broad MW distribution, avg MW $2 \times 10^5$ g/mol, charge density—6.2 meq/g; dose—2 mg/g dry pulp WPADD) APAM—(avg MW $3 \times 10^6$ g/mol, dose—0.2, 1.00, 5.00 mg/g dry pulp for WPA.2AP, WPA1AP, WPA5AP). '*' Represents Pulmac & CSF measurements as before.

The retention aid causes pulp flocculation by a patching mechanism and results in a decrease in the specific surface area and permeability. Drainage is increased as indicated by the gravity drainage curves as well as the freeness (measured as CSF). The optimal parameter set pursuant to this invention is able to follow the drop in specific surface area and agrees with the trend reflected by independent Pulmac measurements as shown in this table.

Table VII shows the consequence of addition of anionic Poly Acrylamide (APAM) to the above system to bring about bridging flocculation.

TABLE VII

| Pulp | $S_w$ | $v_f$ | m | n | CSF |
|---|---|---|---|---|---|
| DPA-0 | 27,000 | 1.22 | 0.00114 | 0.440 | 553 |
| * | 28,515 | 1.22 | 0.00081 | 0.479 | 622 |
| DPADD | 24,000 | 1.07 | 0.00110 | 0.442 | 566 |
| * | 25,266 | 1.07 | 0.00072 | 0.510 | 640 |
| DPA.1AP | 21,000 | 1.14 | 0.00116 | 0.434 | 596 |
| * | 22,474 | 1.14 | 0.00087 | 0.491 | 647 |
| DPA.3AP | 19,000 | 1.00 | 0.00124 | 0.420 | 625 |
| * | 18,715 | 1.00 | 0.00079 | 0.502 | 662 |
| DPA1.7AP | 26,000 | 1.16 | 0.00110 | 0.444 | 522 |
| * | 28,236 | 1.16 | 0.00077 | 0.506 | 630 |

Wherein pulp parameters were determined by optimal drainage curve analysis, Prince Albert Softwood (Bleached Kraft), decrilled using 150 mesh (105 μm opening) screens. Pulp flocculated by addition of PolyDADMAC followed by Anionic Poly Acrylamide (APAM). DADMAC—(broad MW distribution, avg MW $2 \times 10^5$ g/mol, charge density—6.2 meq/g; dose—0.70 mg/g dry pulp DPADD) APAM—(avg MW $3 \times 10^6$ g/mol, dose 0.07, 0.35, 1.74 mg/g dry pulp for DPA.1AP, DPA.3AP, DPA1.7AP). '*' represents Pulmac & CSF measurements as before.

The specific surface area decreases steadily as shown in this table and in fact at the highest dosage level, some redispersion of the pulp seems to occur. Drainage is hampered at high dosage and the specific surface area increases again. The optimal dosage of the polymer for best drainage is indicated at the maximum in the specific surface area as shown in this table. Good correspondence between the Pulmac and the drainage parameters can be found.

To summarize, the pulp tester and analysis method presented herein are capable of determining an optimal parameter set of $S_w$, $v_f$, m, n for a given pulp by analyzing its gravity drainage curve. This parameter set is unique. As shown above, the set describes gravity drainage of the pulp under variation in consistency as well as gravity drainage configuration geometry (e.g., vessel heights, pressure differentials, etc.). The specific surface area strongly characterizes the permeability of the pulp. It drifts higher or lower depending upon the flocculation state of the pulp. Thus, it can be used as an indicator measure of flocculation state—possibly tuning retention or drainage aid dosages. The specific surface area also characterizes the drainage of refined pulps to different extents. Refining changes the area and thus surface area can also be used as a measure to control the operation of pulp refiners. Judicious application of this technique in a repeated fashion on pulps which are fractionated or which can undergo fractionation results in a measure of the fines content of the pulp. The fractional surface area attributable to the fines fraction can be utilized in place of the mass basis fines fraction in many situations directly. Finally, it is possible to obtain a measure of the pulp's wet fiber flexibility (wet fiber elastic modulus) by measuring the compressibility parameters and suitably correlating them.

While the invention has been described in detail herein in accordance with certain preferred embodiments thereof, many modifications and changes therein may be effected by those skilled in the art. Accordingly, it is intended by the appended claims to cover all such modifications and changes as fall within the true spirit and scope of the invention.

I claim:

1. A method for controlling a papermaking process having a control variable and employing a pulp suspension, said method comprising:

(a) establishing a test column having said pulp suspension therein and monitoring pulp suspension height in said test column as a function of time while allowing pulp suspension drainage from the test column;

(b) determining at least one parameter representative of at least one of permeability or compressibility of the pulp suspension utilizing said monitored height as a function of time of the pulp suspension within the test column, wherein said at least one parameter comprises at least one of a specific surface area ($S_w$), specific volume ($v_f$), compressibility constant m and compressibility constant n for the pulp suspension; and (c) employing said at least one parameter representative of at least one of permeability or compressibility of the pulp suspension as feedback to adjust the control variable of the papermaking process to maintain at least one of permeability or compressibility of the pulp suspension near a predefined set point.

2. The method of claim 1, wherein said determining (b) comprises determining each of said $S_w$, $v_f$, m & n.

3. The method of claim 1, further comprising establishing and monitoring pulp suspension height as a function of time in at least two test columns, each test column having a different sized screen disposed in a lower portion thereof for allowing different sized fibers in the pulp suspension to pass therethrough, and wherein said determining (b) comprises determining a difference in specific surface area ($\Delta S_w$) between the fibers retained by the screens in the at least two columns, wherein said $\Delta S_w$ is a measure of the specific surface area attributable to fines in the pulp suspension.

4. The method of claim 1, wherein said determining (b) comprises employing a computer to obtain a best fitting theoretical model of height as a function of time compared with said monitored height as a function of time, said at least one parameter representative of permeability or compressibility comprising a parameter of said best fitting theoretical model.

5. The method of claim 1, wherein said monitoring (a) comprises employing an ultrasonic sensor to monitor said pulp suspension height in said test column as a function of time.

6. The method of claim 1, further comprising simultaneous with said monitoring (a) applying a pressure or a vacuum to said pulp suspension disposed within said test column.

7. The method of claim 1, wherein the papermaking process includes a refiner, and wherein said employing (c) comprises employing said at least one parameter representative of permeability or compressibility of the pulp suspension as a feedback signal to adjust at least one of power input to the refiner, refiner blade gap and RPMs of the refiner.

8. The method of claim 1, wherein said method comprises an online method for automatically controlling the papermaking process through feedback adjustment of the control variable in accordance with the at least one parameter representative of permeability or compressibility of the pulp suspension, said online method being carried out by the operation of a computer.

9. The method of claim 1, further comprising allowing pressure on the pulp suspension within the test column to vary during said monitoring (a).

10. A computer-implemented method for determining at least one parameter representative of at least one of permeability or compressibility of a pulp suspension within a papermaking process, said method comprising:

(a) monitoring instantaneous heights of pulp suspension within a test column under varying pressure conditions while allowing drainage of the pulp suspension from the test column; and (b) determining the at least one parameter representative of at least one of permeability or compressibility of the pulp suspension utilizing said monitored instantaneous heights.

11. The method of claim 10, wherein said determining (b) comprises determining at least one of a specific surface area ($S_w$), specific volume ($v_f$), compressibility constant m and compressibility constant n for the pulp suspension.

12. The method of claim 11, wherein said determining (b) comprises automatically determining each of said $S_w$, $v_f$, m & n.

13. The method of claim 10, further comprising establishing pulp suspension in at least two test columns and monitoring the instantaneous heights of the pulp suspension in the at least two test columns while allowing pulp suspension drainage from the at least two test columns, each test column having a different sized screen disposed in a lower portion thereof for allowing different sized fibers in the pulp suspension to pass therethrough, and wherein said determining (b) comprises determining a difference in at least one of a specific surface area, specific volume, compressibility constant m and compressibility n between the fibers retained by the screens in the at least two columns, wherein said difference is attributable to the fines in the pulp suspension.

14. The method of claim 10, further comprising applying a varying pressure or vacuum to the pulp suspension in the test column simultaneous with said monitoring (a) of instantaneous heights of the pulp suspension in the test column.

15. The method of claim 10, in combination with a method for controlling the papermaking process, wherein the papermaking process has a control variable, said method for controlling including employing said at least one parameter representative of permeability or compressibility of the pulp suspension as feedback to adjust the control variable of the papermaking process to maintain a pulp suspension characteristic near a predefined set point.

16. A method for characterizing fines in a pulp suspension of a papermaking process, said method comprising:

(a) providing at least two test columns having different size screens for removal of fibers from the pulp suspension, one of said screens being sized to allow fines to pass therethrough and one of said screens being sized to prevent fines from passing therethrough;

(b) establishing said pulp suspension within each of said at least two columns;

(c) monitoring instantaneous height of the pulp suspensions within said at least two columns under varying pressure conditions while allowing drainage of said pulp suspensions from said at least two columns;

(d) determining a value for a pulp suspension parameter from the pulp suspensions in each of said at least two columns; and (e) determining a difference between the pulp suspension parameters of said determining (d), wherein said difference is representative of fines in the pulp suspension.

17. The method of claim 16, wherein said pulp suspension parameter comprises one of a specific surface are ($S_w$), specific volume ($v_f$), compressibility constant m and compressibility constant n.

18. A test apparatus for determining at least one parameter representative of at least one of permeability or compressibility of a pulp suspension, said apparatus comprising:

a test column for containing said pulp suspension, said test column including a screen in a lower portion thereof for filtering fibers from said pulp suspension;

a sensor for monitoring height of the pulp suspension within said test column as a function of time while allowing pulp suspension drainage from the test column, said sensor providing output signals each representative of an instantaneous height of the pulp suspension within the test column under varying pressure conditions; and processor means coupled to said sensor for receiving said output signals and for determining therefrom the at least one parameter representative of at least one of permeability or compressibility of the pulp suspension, wherein said at least one parameter comprises at least one of a specific surface area ($S_w$), specific volume ($v_f$), compressibility constant m and compressibility constant n for the pulp suspension.

19. The apparatus of claim 18, wherein said processor means comprises means for automatically determining each of said $S_w$, $v_f$, m & n.

20. The apparatus of claim 18, wherein said test column comprises a first test column and wherein said apparatus further includes a second test column for containing said pulp suspension, said second test column including a second screen in the lower portion thereof for filtering fibers from said pulp suspension, said second screen being of different size than said screen of said first test column, and wherein said sensor comprises a first sensing means and a second sensing means, associated with said first test column and said second test column, respectively, for providing output signals to said processor means, and wherein said processor means further comprises means for determining a difference in at least one of a specific surface area, specific volume, compressibility constant m and compressibility constant n between the fibers retained by the screens of the first test column and the second test column, wherein said screens of the first test column and the second test column are sized such that said difference is attributable to the fines in the pulp suspension.

21. The apparatus of claim 18, wherein said sensor comprises an ultrasonic ranging sensor disposed adjacent to said test column.

22. The apparatus of claim 18, further comprising means for applying a varying pressure or a varying vacuum against the pulp suspension in the test column simultaneous with said sensor's monitoring of height of the pulp suspension in the test column as a function of time.

23. The apparatus of claim 18, in combination with a papermaking system, wherein the papermaking system includes a refiner with at least one control variable, and said apparatus further comprises feedback means for employing said at least one parameter representative of permeability or compressibility of the pulp suspension as feedback from the test apparatus to adjust the control variable of the refiner to maintain a pulp suspension characteristic near a predefined set point.

24. The apparatus of claim 23, wherein said feedback means comprises means for employing said at least one parameter representative of permeability or compressibility of the pulp suspension as a feedback signal to adjust at least one of power input to the refiner, refiner blade gap, and RPMs of the refiner.

* * * * *

UNITED STATES PATENT AND TRADEMARK OFFICE
CERTIFICATE OF CORRECTION

PATENT NO. : 5,954,922

DATED : September 21, 1999

INVENTOR(S) : Ramarao

Page 1 of 2

It is certified that error appears in the above-identified patent and that said Letters Patent is hereby corrected as shown below:

Col. 9, line 26, please insert

--14b. Call R[0,1]

15. Compare $X_k^2$ with $X_{k-1}^2$

If $X_k^2 < X_{k-1}^2$ and $R < Z$

Acccept $\underline{x_k}$.
Increment number $N_{acc}$, wherein $N_{acc}$ equals the number of times of acceptance.
Else
Reject.

16. Choose $X_{min_o}^2 = Min\left[X_{Min_o}^2, X_k^2\right]$.

Continue until $K = N_{400}$.
(Go to step (12)).

17. Determine the comparison parameter
$\mu' = N_{acc}/N_{400}$.

18. Compare $\mu'$ with $\mu_c$
where:

UNITED STATES PATENT AND TRADEMARK OFFICE
CERTIFICATE OF CORRECTION

PATENT NO. : 5,954,922
DATED : September 21, 1999
INVENTOR(S) : Ramarao

It is certified that error appears in the above-identified patent and that said Letters Patent is hereby corrected as shown below:

19. $\mu_c = 0.5$ (Arbitrarily chosen).

20. Set $\Delta = 0.1$, and
    If $\mu > \mu_c + \Delta$
    or $\mu < \mu_c - \Delta$,
    Then go to step (12) and repeat.

21. Else,
    If $T < T_{min} = 10^{-5}$ and step (23) is satisfied, parameters are at the minimum.

22. Else,
    $T_{new} = T_{old} * f$, where $f$ is chosen as 0.85.
    Go to step (12), and increment "Loop Count".

23. Check if "Loop Count" is greater than 4.--

Signed and Sealed this

Twenty-fifth Day of April, 2000

Q. TODD DICKINSON

*Attest:*

*Attesting Officer*        *Director of Patents and Trademarks*